United States Patent [19]
Siegenthaler

[11] 3,944,635
[45] Mar. 16, 1976

[54] APPARATUS FOR HUMIDIFYING A GAS

[75] Inventor: Peter Siegenthaler, Niederscherli, Switzerland

[73] Assignee: Carba Limited, Bern, Switzerland

[22] Filed: Apr. 16, 1975

[21] Appl. No.: 568,578

[30] Foreign Application Priority Data
Apr. 19, 1974 Switzerland.......................... 5417/74

[52] U.S. Cl. .................. 261/62; 128/194; 239/338; 261/78 A; 261/DIG. 65
[51] Int. Cl.² ................. A61M 11/02; A61M 11/06; A61M 15/00
[58] Field of Search .... 261/78 A, 62, 118, DIG. 65; 128/194, 188, 193; 239/338

[56] References Cited
UNITED STATES PATENTS
| | | |
|---|---|---|
| 3,395,703 | 8/1968 | Chouinard et al. ................ 239/338 |
| 3,664,337 | 5/1972 | Lindsey et al. ..................... 128/194 |
| 3,744,722 | 7/1973 | Burns................................. 128/194 |
| 3,836,079 | 9/1974 | Huston............................... 128/194 |

OTHER PUBLICATIONS
Baro Parker Co., Moduflex System, Apr. 1974, p. 3, see Nebulizer Design figure.

*Primary Examiner*—Tim R. Miles
*Assistant Examiner*—Gregory N. Clements
*Attorney, Agent, or Firm*—Michael J. Striker

[57] ABSTRACT

An apparatus for humidifying a gas, such as oxygen to be supplied for medicinal purposes, comprises a container for the humidifying liquid (e.g. water) and a mist-producing element which uses the flow of gas to induce a spray of the liquid into the gas space in the container in dependence upon the rate of gas flow.

4 Claims, 4 Drawing Figures

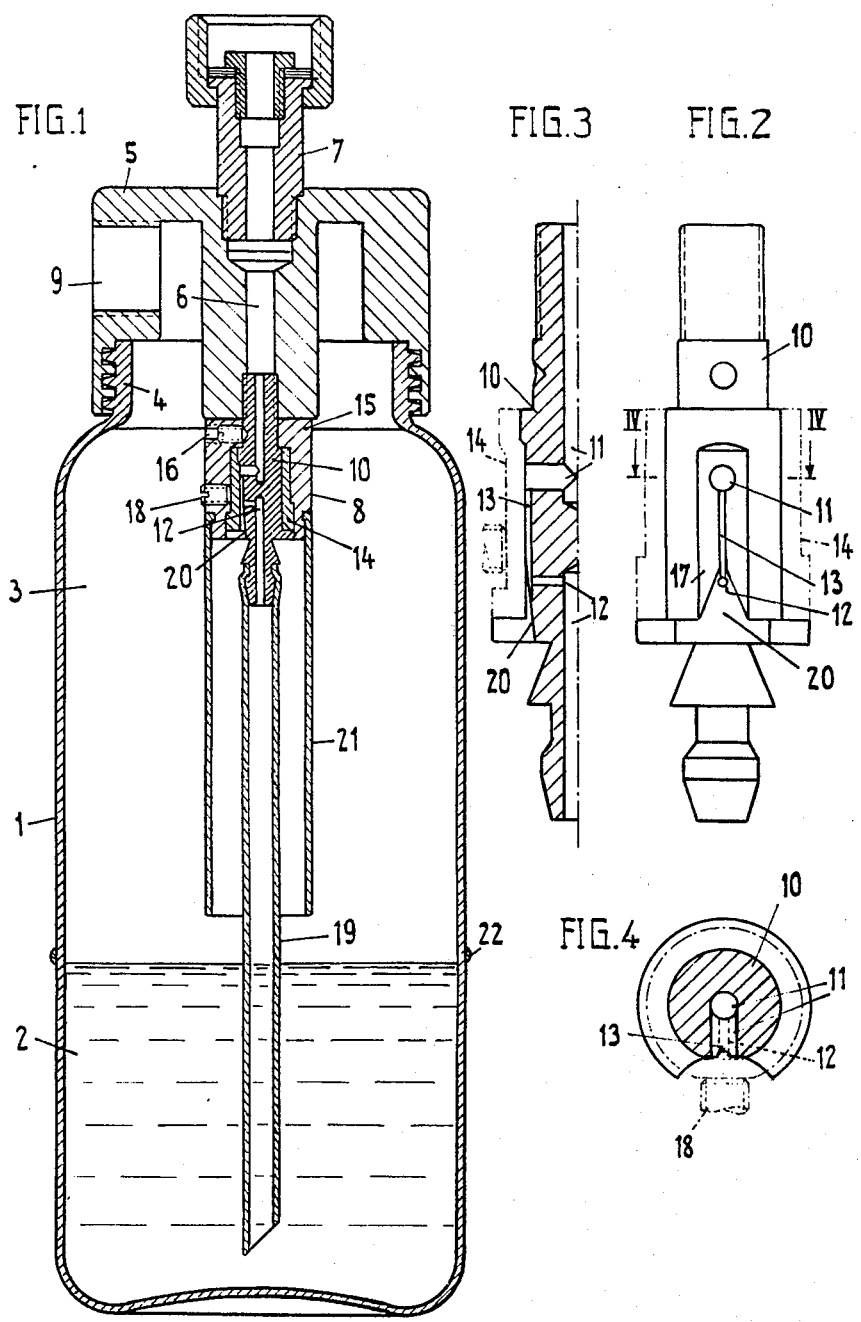

APPARATUS FOR HUMIDIFYING A GAS

BACKGROUND OF THE INVENTION

1. Field of the Invention

The invention relates to an apparatus for humidifying a gas, such as oxygen for example, which apparatus comprises a container for the humidifying liquid and an inlet duct, leading into the container, for the gas which is to be humidifed.

2. Description of the Prior Art

Since oxygen used for medicinal purposes is stored in a very dry condition in steel cylinders from which it can be taken in controlled doses, the administration of such oxygen to patients would result in dangerous drying of the respiratory passages. For the purpose of humidification the gaseous oxygen is therefore passed before administration through an apparatus in which it is brought to a sufficient degree of relative humidity.

With customary apparatus of this kind however it has been found that with an increasing flow of gas per unit of time the attainable degree of relative gas humidity decreases so considerably that the respiratory passages of the patient nevertheless dry out.

SUMMARY OF THE INVENTION

The invention seeks to provide an apparatus for humidifying, in particular, dry oxygen gas, which is so constructed that the adjustable degree of humidification is achieved independently of the flow of gas per unit of time.

According to the present invention an apparatus for humidifying a gas comprises a container for the humidifying liquid and a supply duct, entering the said container, for the gas which is to be humidified, wherein the gas supply duct terminates in the container in a mist-producing element which comprises a core piece, an elastic jacket which lies tightly against the peripheral surface of the latter, and a sleeve surrounding the jacket, the supply duct entering the core piece and opening into a longitudinal groove on the peripheral surface of the core piece, which groove leads out into the container at one end of the jacket, while in the middle portion of its length a liquid suction duct entering the core piece from the liquid-containing region of the container opens transversely into the groove and in the sleeve there is dispoed opposite the groove an adjusting screw by means of which the cross-section of the groove for the passage of the gas can be adjusted, with the aid of the jacket, just before the opening of the liquid suction duct.

BRIEF DESCRIPTION OF THE DRAWINGS

FIG. 1 is a vertical axial section through the gas humidifying apparatus;

FIG. 2 a side-view of the core piece of the mist-producing element of the apparatus;

FIG. 3 an axial half-section corresponding to FIG. 2, and

FIG. 4 a cross-section on the line IV—IV in FIG. 2.

DETAILED DESCRIPTION OF THE INVENTION

The apparatus shown comprises a transparent cylindrical bottle 1 which serves as container for humidifying water 2 and humidified oxygen gas 3 and which has a tightly closing cover 5 screwed onto its neck 4. The cover 5 has an axial bore 6, to which are connected a connection 7, screwed in from the outside of the cover, for the admission of oxygen gas, and a mist-producing element 8 screwed in on the inside of the cover. The cover 5 is provided with a discharge bore 9 for humidified oxygen, the bore having a lateral outlet.

The mist-producing element 8 comprises a core piece 10 having two bores 11 and 12 for oxygen and humidifying water respectively, which bores enter axially on opposite sides and pass out radially and on the outer surface of the core piece lead into an axially parallel groove 13 at an axial distance from one another. The mist-producing element 8 also comprises an elastic jacket 14, which for example is made of rubber and which over a length slightly greater than the groove 13 lies tightly against the peripheral surface of the core piece 10, and a sleeve 15 which surrounds the jacket 14 and is secured against axial displacement on the core piece 10 by means of a set screw 16. The peripheral surface of the core piece 10, which is enclosed by the jacket 14, is cylindrical in the proximity of the groove 13 with the exception of a flattened portion 17.

By means of an adjusting screw 18 screwed from outside into the sleeve 15, the jacket 14 can be pressed to a greater or lesser extent against the groove 13 near the substantially capillary radial portion of the bore 12, between the mouths of the two bores 11 and 12 leading into the groove 13, so that the cross-section of the groove can be narrowed accordingly. The speed of flow of the oxygen gas and thus the suction pressure at the outlet of the bore 12 can be controlled in this manner, for the purpose of sucking humidified water through the suction pipe 19 connected to the core piece 10 and through the bore 12, and in order to effect the entraining of this water by the oxygen current and spraying it in the outlet end 20 of the groove 13, which end is widened in wedge shape in the direction of three sides. A drip collector pipe 21 fastened to the core piece 10 and coaxially surrounding the suction pipe 19 extends towards the surface of the water, which at most should stand at the marking 22, and effects the separation of drops of spray water deposited on the wall of the pipe and their return to the humidifying water. In the pipe 21 the expanded oxygen gas is saturated with the $H_2O$ aerosol and passes into the bottle chamber above the humidifying water 2 and then through a slightly conical discharge bore 9 to a connected consumer apparatus.

With the apparatus described, for example with the regulating screw 18 at its optimum setting in dependence on the flow of oxygen, it can be ensured that with a flow of oxygen of 1 liter per minute the reduced pressure produced above the outlet of the bore 12 in the groove 13 will amount to 15 millibars and with a flow of oxygen of 10 liters per minute it will amount to 150 millibars.

I claim:

1. An apparatus for humidifying a gas, which apparatus comprises a container for the humidifying liquid and a supply duct, entering the said container, for the gas which is to be humidified, wherein the gas supply duct terminates in the container in a mist-producing element which comprises a core piece, an elastic jacket which lies tightly against the peripheral surface of the latter, and a sleeve surrounding the jacket, the supply duct entering the core piece and opening into a longitudinal groove on the peripheral surface of the core piece, which groove leads out into the container at one end of the jacket, while in the middle portion of its length a liquid suction duct entering the core piece from the liquid-containing region of the container opens transversely into the groove, and in the sleeve there is disposed opposite the groove an adjusting screw by means of which the cross-section of the groove for the passage of the gas can be adjusted, with the aid of the jacket, just before the opening of the liquid suction duct.

2. An apparatus according to claim 1, wherein the opening of the liquid suction duct into the groove is disposed at the narrow end of a wedge-shaped widened portion of the groove, at which widened portion the side walls and also the bottom of the groove extend obliquely to the longitudinal direction of the groove.

3. An apparatus according to claim 1, wherein the peripheral surface of the core piece is mainly cylindrical but is flattened on both sides of the groove.

4. An apparatus according to claim 1, wherein a drip collection tube extending to the surface of the liquid in the container is connected to the sleeve, and the liquid suction duct outside the core piece is formed by a tube which is connected to the core piece and which extends almost to the bottom of the container.

* * * * *